United States Patent [19]

Ogletree

[11] Patent Number: 4,839,384
[45] Date of Patent: Jun. 13, 1989

[54] METHOD OF INHIBITING ONSET OF OR TREATING MIGRAINE HEADACHE USING A THROMBOXANE A2 RECEPTOR ANTAGONIST

[75] Inventor: Martin L. Ogletree, Newtown, Pa.

[73] Assignee: E. R. Squibb & Sons, Inc., Princeton, N.J.

[21] Appl. No.: 254,899

[22] Filed: Oct. 7, 1988

[51] Int. Cl.$^4$ .................... A61K 31/36; A61K 31/38; A61K 31/41; A61K 31/435
[52] U.S. Cl. .................... 514/277; 514/381; 514/438; 514/465; 514/466
[58] Field of Search ............... 514/381, 438, 465, 466, 514/277

[56] References Cited

FOREIGN PATENT DOCUMENTS 137726  4/1985  European Pat. Off. .
201349  11/1986  European Pat. Off. .
201350  11/1986  European Pat. Off. .
223518  5/1987  European Pat. Off. .

OTHER PUBLICATIONS

Joseph Rajiv et al., "Thromboxane Synthetase Inhibition: Potential Therapy in Migraine," Headache 25:204–207, 1985.

*Primary Examiner*—Stanley J. Friedman
*Attorney, Agent, or Firm*—Burton Rodney

[57] ABSTRACT

A method is provided for inhibiting onset or treating migraine headaches by administering a thromboxane A$_2$ receptor antagonist before of during the migraine which thromboxane A$_2$ receptor antagonist is a 7-oxabicycloheptane prostaglandin analog.

11 Claims, No Drawings

METHOD OF INHIBITING ONSET OF OR TREATING MIGRAINE HEADACHE USING A THROMBOXANE A2 RECEPTOR ANTAGONIST

FIELD OF THE INVENTION

The present invention relates to a method for inhibiting onset of or treating migraine headaches by administering a thromboxane $A_2$ receptor antagonist which is a 7-oxabicyclo prostaglandin analog.

BACKGROUND OF THE INVENTION

European patent application No. 137,426 (Bayer AG) discloses compositions containing 2-thiazolylthio-alkanoic acid derivatives which have thromboxane antagonizing and platelet aggregation inhibiting activity and may be used in treating migraine headaches.

European patent application No. 201,349 (ICI) discloses hydroxyphenyldioxanyl-alkenyl-tetrazole compounds which are useful as thromboxane $A_2$ antagonists in the treatment of ischemic heart disease and cerebrovascular disorders such as migraine headaches.

European patent application No. 201,350 (ICI) discloses hydroxyphenyloxa-thienyl-alkenoic acid derivatives useful as thromboxane-$A_2$ antagonists in treating heart diseases and cerebrovascular disorders such as migraine headaches.

European patent application No. 223,518 (ICI) discloses N-o-hydroxyphenyl-dioxan-cis-yl-hexenoylsulfonamide derivatives useful as antagonists of thromboxane $A_2$ for treating ischemic heart disease and cerebrovascular disease such as migraine headaches.

DESCRIPTION OF THE INVENTION

In accordance with the present invention, a method is provided for inhibiting onset of or treating migraine headaches wherein a therapeutically effective amount of a thromboxane $A_2$ receptor antagonist is systemically administered, such as orally or parenterally, over a prolonged period, whereby frequency and intensity of migraine headaches are significantly reduced.

The term "thromboxane $A_2$ receptor antagonist" as employed herein includes compounds which are so-called thromboxane $A_2$ receptor antagonists, thromboxane $A_2$ antagonists, thromboxane $A_2$/prostaglandin endoperoxide antagonists, TP-receptor antagonists, or thromboxane antagonists except insofar as the compound is solely an inhibitor of thromboxane synthesis.

The thromboxane $A_2$ receptor antagonist employed herein will be a 7-oxabicycloheptane prostaglandin analog and will include 7-oxabicycloheptane substituted diamide prostaglandin analogs as disclosed in U.S. Pat. No. 4,663,336, 7-oxabicycloheptane substituted amino prostaglandin analogs as disclosed in U.S. Pat. No. 4,416,896 and 7-oxabicycloheptane prostaglandin analogs as disclosed in U.S. Pat. No. 4,537,981.

The 7-oxabicycloheptane substituted diamide prostaglandin analogs suitable for use herein, as disclosed in U.S. Pat. No. 4,663,336, have the formula

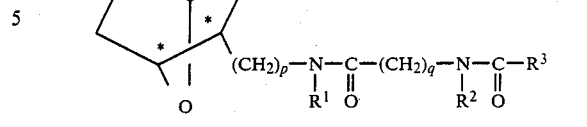

including all stereoisomers thereof, wherein m is 0 to 4; A is —CH=CH— or —CH$_2$—CH$_2$—; n is 1 to 5; Q is —CH=CH—, —CH$_2$,

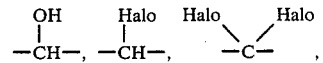

or a single bond; R is CO$_2$H, CO$_2$alkyl, CO$_2$ alkali metal, CO$_2$polyhydroxyamine salt, —CH$_2$OH,

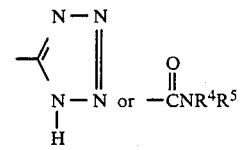

wherein $R^4$ and $R^5$ are the same or different and are H, lower alkyl, hydroxy, lower alkoxy or aryl at least one of $R^4$ and $R^5$ being other than hydroxy and lower alkoxy; p is 1 to 4; $R^1$ is H or lower alkyl; q is 1 to 12; $R^2$ is H or lower alkyl; and $R^3$ is H, lower alkyl, lower alkenyl, lower alkynyl, aryl, arylalkyl, lower alkoxy, arylalkyloxy, aryloxy, amino, alkylamino, arylalkylamino, arylamino,

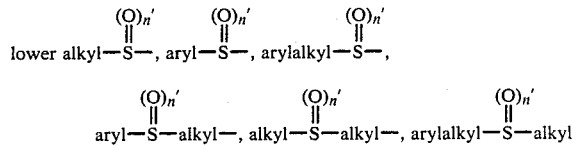

(wherein n' is 0, 1 or 2), alkylaminoalkyl, arylaminoalkyl, arylalkylaminoalkyl, alkoxyalkyl, aryloxyalkyl or arylalkoxyalkyl.

The 7-oxabicycloheptane substituted amino prostaglandin analogs suitable for use herein, as disclosed in U.S. Pat. No. 4,416,896, have the formula

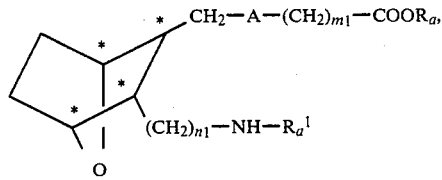

and including all stereoisomers thereof, wherein
A is CH=CH or (CH$_2$)$_2$; m$_1$ is 1 to 8; n$_1$ is 0 to 5, R$_a$ is H or lower alkyl; and R$_a^1$ is lower alkyl, aryl, aralkyl, lower alkoxy, aralkoxy or

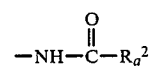

wherein $R_a{}^2$ is lower alkyl, aryl, aralkyl, alkoxy, aryloxy, aralkoxy, alkylamino, arylamino or aralkylamino.

The 7-oxabicycloheptane prostaglandin analogs suitable for use herein, as disclosed in U.S. Pat. No. 4,537,981, have the formula

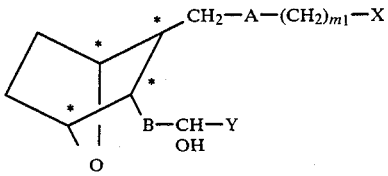

and including all stereoisomers thereof, wherein A and B may be the same or different and A is CH=CH or $(CH_2)_2$; B is CH=CH, C≡C or $(CH_2)_2$; $m_1$ is 1 to 8; X is OH;

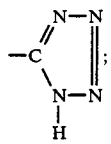

$CO_2R_a$ wherein $R_a$ is H or lower alkyl; or

wherein Z is H, lower alkyl, aryl, $SO_2-Q_1$ (with $Q_1$ being lower alkyl or aryl),

or $OR_b{}^2$ wherein $R_b{}^2$ is H, and Y is alkyl, substituted alkyl; aryl-lower alkyl; alkenyl; alkynyl, aryl; pyridyl; substituted pyridyl; pyridyl-lower alkyl; thienyl, substituted thienyl; thienyl-lower alkyl; cycloalkyl; cycloalkylalkyl; substituted cycloalkylalkyl; or phenoxymethyl.

Preferred examples of thromboxane $A_2$ receptor antagonists which may be employed herein include the 7-oxabicycloheptane compounds disclosed in U.S. Pat. No. 4,537,981, especially, [1S-[1α,2β(5Z),3β(-1E,3R,4S),4α[[-7-[3-(3-hydroxy-4-phenyl-1-pentenyl)-7-oxabicyclo[2.2.1]hept-2-yl]-5-heptenoic acid; the 7-oxabicycloheptane substituted amino-prostaglandin analogs disclosed in U.S. Pat. No. 4,416,896, especially, [1S-[1α,2β,(5Z),3β,4α]]-7-[3-[[2-(phenylamino)carbonyl]hydrazino]methyl]-7-oxabicyclo[2.2.1]hept-2-yl]-5-heptenoic acid; the 7-oxabicycloheptane substituted diamide prostaglandin analogs disclosed in U.S. Pat. No. 4,663,336, expecially, [1S-[1β,2α(5Z),3α,4β]]-7-[3-[[[[(1-oxoheptyl)amino]acetyl]amino]methyl]-7-oxabicyclo[2.2.1]hept-2-yl]-5-heptenoic acid and the corresponding tetrazole, and [1S-[1α,2β(Z),3β,4α]]-7-[3-[[[[(4-cyclohexyl-1-oxobutyl)amino]acetyl]amino]-methyl]-7-oxabicyclo[2.2.1]hept-2-yl]-5-heptenoic acid.

The disclosures of the above-mentioned patents are incorporated herein by reference.

In carrying out the method of the present invention, the thromboxane $A_2$ receptor antagonist may be administered systemically, such as orally or parenterally, to mammalian species, such as monkeys, dogs, cats, rats, humans, etc., during the migraine headache or prior to or after the onset of the migraine headache.

The thromboxane $A_2$ receptor antagonist may be incorporated in a conventional dosage form, such as a tablet, capsule, elixir or injectable. The above dosage forms will also include the necessary carrier material, excipient, lubricant, buffer, antibacterial, bulking agent (such as mannitol), anti-oxidants (ascorbic acid or sodium bisulfite) or the like. Oral dosage forms are preferred, although parenteral forms are quite satisfactory as well.

With regard to such systemic formulations, single or divided doses of from about 0.5 to about 2500 mg, preferably from about 5 to 200 mg/one to four times daily, may be administered in systemic dosage forms as described above for a prolonged period, that is, for as long as the potential for onset of a migraine headache remains or the symptoms of a migraine headache continue. Sustained release forms of such formulations which may provide such amounts biweekly, weekly, monthly and the like may also be employed. A dosing period of as long as 6 weeks may be required to achieve minimal benefit.

The following Examples represent preferred embodiments of the present invention.

EXAMPLE 1

An injectable solution of thromboxane $A_2$ receptor antagonist for intravenous use in treating or preventing onset of migraine headache is produced as follows:

| | |
|---|---|
| [1S—[1α,2β(5Z),3β,4α]]-7-[3-[[2-(phenylamino)carbonyl]hydrazino]-methyl]-7-oxabicyclo[2·2·1]hept-2-yl]-5-heptenoic acid (SQ 29,548) | 2500 mg |
| Methyl paraben | 5 mg |
| Propyl paraben | 1 mg |
| Sodium chloride | 25 g |
| Water for injection qs. | 5 l. |

The thromboxane $A_2$ receptor antagonist, preservatives and sodium chloride are dissolved in 3 liters of water for injection and then the volume is brought up to 5 liters. The solution is filtered through a sterile filter and aseptically filled into presterilized vials which are then closed with presterilized rubber closures. Each vial contains a concentration of 75 mg of active ingredient per 150 ml of solution.

EXAMPLE 2

An injectable for use in inhibiting onset of or treating migraine headache is prepared as described in Example 1 except that the thromboxane $A_2$ receptor antagonist employed is [1S-[1α,2β(5Z),3β(1E,3R,4S),4α]]-7-[3-(3-hydroxy-4-phenyl-1-pentenyl)-7-oxabicyclo[2.2.1]hept-2-yl]-5-heptenoic acid (SQ 28,668).

EXAMPLE 3

An injectable solution of thromboxane $A_2$ receptor antagonist for use in inhbiting onset of or treating migraine headache containing [1S-[1β,2α(5Z),3α,4β]]-7-[3-[[[[(1-oxoheptyl)-amino]acetyl]amino]methyl]-7-oxabicyclo[2.2.1]-hept-2-yl]-5-heptenoic acid (SQ 30,741) as the thromboxane $A_2$ receptor antagonist is prepared as described in Example 1.

EXAMPLE 4

An injectable for use in inhibiting onset of or treating migraine headache is prepared as described in Example 1 except that the thromboxane $A_2$ receptor antagonist employed is [1S-[1α,2β(Z),3β,4α]]-7-[3-[[[[(4-cyclohexyl-1-oxobutyl)amino]acetyl]amino]methyl]-7-oxabicyclo[2.2.1]hept-2-yl]-5-heptenoic acid.

EXAMPLE 5

A thromboxane $A_1$ antagonist formulation suitable for oral administration for use in inhibiting onset of or treating migraine headache is set out below.

1000 tablets each containing 400 mg of thromboxane $A_2$ receptor antagonist are produced from the following ingredients.

| | |
|---|---|
| [1S—[1β,2α(5Z),3α,4β]]-7-[3-[[[[(1-Oxoheptyl)amino]acetyl]amino]methyl]-7-oxabicyclo[2.2.1]hept-2-yl]-5-heptenoic acid (SQ 30,741) | 400 g |
| Corn starch | 50 g |
| Gelatin | 7.5 g |
| Avicel (microcrystalline cellulose) | 25 g |
| Magnesium stearate | 2.5 g |

The thromboxane $A_2$ receptor antagonist and corn starch are admixed with an aqueous solution of the gelatin. The mixture is dried and ground to a fine powder. The Avicel and then the magnesium stearate are admixed with the granulation. This is then compressed in a tablet to form 1000 tablets each containing 400 mg of active ingredient.

EXAMPLE 6

A thromboxane $A_2$ antagonist tablet formulation for use in inhibiting onset of or treating migraine headache is prepared as described in Example 5 except that SQ 29,548 is employed as the thromboxane $A_2$ receptor antagonist in place of SQ 30,741.

EXAMPLE 7

A thromboxane $A_2$ antagonist tablet formulation for use in inhibiting onset of or treating migraine headache is prepared as described in Example 5 except that SQ 28,668 is employed in placed of SQ 30,741.

EXAMPLE 8

The following experiment was carried out to show the effectiveness of the thromboxane $A_2$ receptor antagonist SQ 29,548 in neutralizing adverse effects of thromboxane mimetic U-46,619 9,11-dideoxy-9α,11α-methanoepoxy $PGF_{2α}$ in the mouse brain.

It is known that thromboxane may be involved in the pathagenesis of migraine, Headache 25: 204–207, 1985.

Intravenous injection of thromboxane mimetics, e.g., U-46,619, causes thromboxane receptor dependent paralysis and death in mice (Myers et al, J. Pharmacol. Exp. Therap. 224: 369, 1983; Harris et al, Drugs of the Future 13: 153, 1988). To explore the mechanism(s) of these responses, injected mice were injected with Evans Blue dye (20 mg/kg, i.v.) and 5 minutes later challenged with U-46,619 (50 μg/kg, i.v.) or vehicle. Ten minutes later the mice were sacrificed, the arterial circulation flushed with saline, selected tissues including brain weighed, and Evans Blue dye content of each tissue extracted and measured. The dye bound completely to plasma proteins and served as a marker of the distribution space for plasma proteins the size of albumin (~68 K daltons). Compared to vehicle, U-46,619 increased hematocrit (vehicle: 49±1; U-46,619: 53±1) and visibly increased dye content in brain. Treatment with the thromboxane receptor antagonist, SW 29,548 before U-46,619 challenge, inhibited in a dose-related manner both changes in hematocrit and dye accumulation in the brain. Brain tissue dye contents are summarized in the table.

| Evans Blue Content in ng/mg Wet Tissue (Mean ± SEM, n = 6–7) | |
|---|---|
| | Brain |
| Saline + Vehicle | 2 ± 0 |
| Saline + U-46,619 | 13 ± 3 |
| SQ29,548 + U-46,619 | 2 ± 0 |

Thus, U-46,619 caused thromboxane receptor dependent, tissue selective increases in Evans Blue content in mice. These findings support a role for thromboxane receptors in regulation of vascular permeability of the blood-brain barrier. U-46,619-induced sudden death is associated with a major change in cerebral vascular permeability.

The thromboxane $A_2$ receptor antagonist SQ 29,548 neutralized the adverse effects caused by the thromboxane mimetic U-46,619 and thus it is expected that it is useful in treating migraine headaches.

What is claimed is:

1. A method for inhibiting onset of or treating migraine headache in a mammalian species, which comprises administering to a mammalian species in need of such treatment an effective amount of a thromboxane $A_2$ receptor antagonist over a prolonged period of treatment to reduce frequency and/or severity of migraine headaches during such period of treatment, which thromboxane $A_2$ receptor antagonist is a 7-oxabicycloheptane prostaglandin analog.

2. The method as defined in claim 1 wherein the 7-oxabicycloheptane prostaglandin analog is a 7-oxabicycloheptane substituted diamide prostaglandin analog or a 7-oxabicycloheptane substituted amino prostaglandin analog.

3. The method as defined in claim 1 wherein the 7-oxabicycloheptane prostaglandin analog has the formula

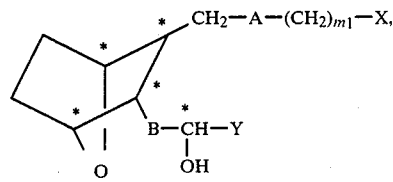

and including all stereoisomers thereof, wherein
A and B may be the same or different and A is $CH=CH$ or $(CH_2)_2$; B is $CH=CH$, $C\equiv C$ or $(CH_2)_2$; $m_1$ is 1 to 8; X is OH;

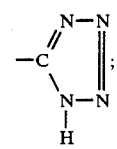

$CO_2R_a$ wherein $R_a$ is H or lower alkyl; or

wherein Z is H, lower alkyl, aryl, $SO_2-Q_1$ (with $Q_1$ being lower alkyl or aryl),

or $OR_b{}^2$ wherein $R_b{}^2$ is H, and Y is alkyl; substituted alkyl; aryl-lower alkyl; alkenyl; alkynyl; aryl; pyridyl; substituted pyridyl; pyridyl-lower alkyl; thienyl, substituted thienyl; thienyl-lower alkyl; cycloalkyl; cycloalkylalkyl; substituted cycloalkylalkyl; or phenoxymethyl.

4. The method as defined in claim 2 wherein the 7-oxabicycloheptane substituted diamide prostaglandin analog has the formula

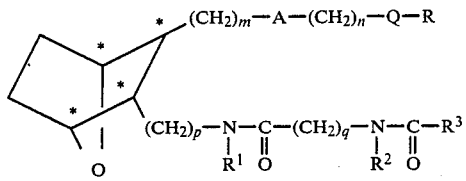

including all stereoisomers thereof, wherein m is 0 to 4; A is $-CH=CH-$ or $-CH_2-CH_2-$; n is 1 to 5; Q is $-CH=CH-$, $-CH_2$,

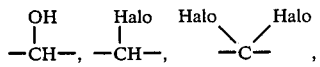

or a single bond; R is $CO_2H$, $CO_2$alkyl, $CO_2$ alkali metal, $CO_2$polyhydroxyamine salt, $-CH_2OH$,

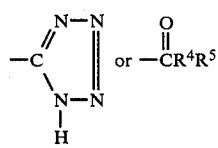

wherein $R^4$ and $R^5$ are the same or different and are H, lower alkyl, hydroxy, lower alkoxy or aryl at least one of $R^4$ and $R^5$ being other than hydroxy and lower alkoxy; p is 1 to 4; $R^1$ is H or lower alkyl; q is 1 to 12; $R^2$ is H or lower alkyl; and $R^3$ is H, lower alkyl, lower alkenyl, lower alkynyl, aryl, arylalkyl, lower alkoxy, arylalkyloxy, aryloxy, amino, alkylamino, arylalkylamino, arylamino,

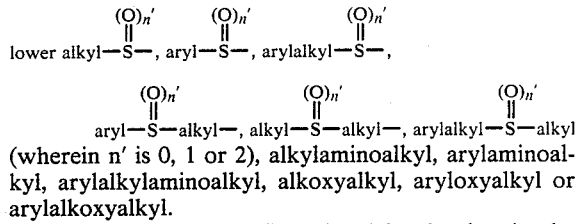

(wherein n' is 0, 1 or 2), alkylaminoalkyl, arylaminoalkyl, arylalkylaminoalkyl, alkoxyalkyl, aryloxyalkyl or arylalkoxyalkyl.

5. The method as defined in claim 2 wherein the 7-oxabicycloheptane substituted amino prostaglandin analog has the formula

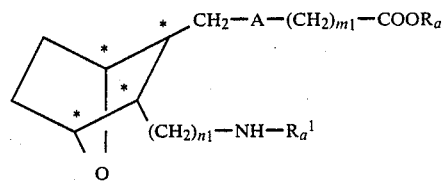

and including all stereoisomers thereof, wherein A is $CH=CH$ or $(CH_2)_2$; $m_1$ is 1 to 8; $n_1$ is 0 to 5, $R_a$ is H or lower alkyl; and $R_a{}^1$ is lower alkyl, aryl, aralkyl, lower alkoxy, aralkoxy or

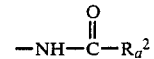

where $R_a{}^2$ is lower alkyl, aryl, aralkyl, alkoxy, aryloxy, aralkoxy, alkylamino, arylamino or aralkylamino.

6. The method as defined in claim 1 wherein the thromboxane $A_2$ receptor antagonist is [1S-[1α,2β(5Z),3β(1E,3R,4S),4α]]-7-[3-(3-hydroxy-4-phenyl-1-pentenyl)-7-oxabicyclo[2.2.1]hept-2-yl]-5-heptenoic acid.

7. The method as defined in claim 1 wherein the thromboxane $A_2$ receptor antagonist has the name [1S-[1β,2α(5Z),3α,4β]]-7-[3-[[[[(1-oxoheptyl)amino]acetyl]amino]methyl]-7-oxabicyclo[2.2.1]hept-2-yl]-5-heptenoic acid or the corresponding tetrazole.

8. The method as defined in claim 1 wherein the thromboxane $A_2$ receptor antagonist has the name [1S-[1α,2β(Z),3β,4α]]-7-[3-[[[[(4-cyclohexyl-1-oxobutyl)amino]acetyl]amino]methyl]-7-oxabicyclo[2.2.1]hept-2-yl]-5-heptenoic acid.

9. The method as defined in claim 1 wherein the thromboxane $A_2$ receptor antagonist has the name [1S-[1α,2β(5Z),3β,4α]]-7-[3-[[2-(phenylamino)carbonyl]hydrazino]methyl]-7-oxabicyclo[2.2.1]hept-2-yl]-5-heptenoic acid.

10. The method as defined in claim 1 wherein the thromboxane $A_2$ receptor antagonist is administered orally or parenterally.

11. The method as defined in claim 1 wherein the thromboxane receptor antagonist is administered in single or divided doses of from about 0.5 to about 2500 mg/one to four times daily.

* * * * *